United States Patent [19]

Tesch et al.

[11] Patent Number: 4,559,398

[45] Date of Patent: Dec. 17, 1985

[54] CURABLE EPOXY RESINS

[75] Inventors: Helmut Tesch, Birkenheide; Andreas Henne, Neustadt; Manfred Heym, Weisenheim; Herbert Stutz, Karlsruhe, all of Fed. Rep. of Germany

[73] Assignee: BASF Aktiengesellschaft, Fed. Rep. of Germany

[21] Appl. No.: 636,236

[22] Filed: Jul. 31, 1984

[30] Foreign Application Priority Data

Aug. 2, 1983 [DE] Fed. Rep. of Germany ....... 3327823

[51] Int. Cl.$^4$ .............................................. C08G 59/68
[52] U.S. Cl. ...................... 528/94; 525/504; 528/117; 528/365; 528/408
[58] Field of Search ................ 528/94, 117, 407, 408; 525/504, 365

[56] References Cited

U.S. PATENT DOCUMENTS 3,329,652 7/1967 Christie .................................. 260/47
4,436,892 3/1984 Zondler et al. ...................... 528/117

FOREIGN PATENT DOCUMENTS 1050679 4/1964 United Kingdom .

*Primary Examiner*—Earl Nielsen
*Attorney, Agent, or Firm*—Keil & Weinkauf

[57] ABSTRACT

A curable composition consisting of
A. 100 parts by weight of an epoxy resin,
B. from 4 to 100 parts by weight of a conventional curing agent for epoxy resins, and
C. from 0.1 to 5 parts by weight of an N-acylimidazole which possesses an aromatic acyl component which is substituted at the two positions ortho to the carbonyl group can be used to produce moldings, coatings, finishes, adhesives and composite fiber materials.

7 Claims, No Drawings

CURABLE EPOXY RESINS

The present invention relates to epoxy resins which contain a substituted N-acylimidazole as an accelerator, in combination with a conventional curing agent.

It has been disclosed, for example in GB-A-1,050,679, that imidazoles react very rapidly with epoxy resins at elevated temperatures to give moldings possessing good physical properties. The imidazoles initiate anionic polymerization of the epoxy resins, with the result that a three-dimensional network comprising polyether structures is formed.

It has also been disclosed, for example in U.S. Pat. No. 3,329,652, that small amounts of imidazoles can act as curing agents and accelerate the reaction of epoxy resins with polycarboxylic anhydrides.

In both cases, the mixtures have the disadvantage that they have only a short shelf life at room temperature and at moderately elevated temperatures.

It is an object of the present invention to provide a curable resin composition based on epoxy resins, which has a relatively long shelf life at room temperature and moderately elevated temperatures, and undergoes rapid curing, giving moldings with good mechanical properties, only when the temperature is increased greatly.

We have found that this object is achieved if an N-acylimidazole which possesses an aromatic acyl component which is substituted at the two positions ortho to the carbonyl group is used as an accelerator for epoxy resins containing conventional curing agents.

U.S. Pat. No. 4,436,892 describes N-acylimidazoles in which the aromatic acyl group is halogen-substituted or nitro-substituted, and these imidazoles are said to be useful curing agents for epoxy resins. However, we have found that resin systems of this type, too, do not have a sufficiently long shelf life.

The present invention relates to curable resin compositions containing

A. 100 parts by weight of an epoxy resin,
B. from 4 to 100 parts by weight of a conventional curing agent for epoxy resins, and
C from 0.1 to 5 parts by weight of an N-acylimidazole of the formula I or II.

Epoxy resins are low molecular weight or high molecular weight compounds containing terminal epoxide groups, epoxide side groups, or epoxide groups incorporated into cyclic systems. They can be liquid, semi-solid or solid. Preferred compounds are those which contain more than one epoxide group per molecule, and preferred epoxy resins are reaction products of polyfunctional alcohols, phenols, cycloaliphatic carboxylic acids, aromatic amines or aminophenols with epichlorohydrin, as well as cycloaliphatic epoxides and cycloaliphatic epoxideesters. Mixtures of different epoxy resins may also be used. Bisphenol A diglycidyl ether, tetraglycidyldiaminodiphenylmethane and epoxidized novolaks are particularly preferred. The resins can contain the conventional diluents, such as phenyl glycidyl ether or butyl glycidyl ether.

The N-acylamidazoles used according to the invention, of the formulae I and II, are known. Their preparation is described in, for example, Liebigs Ann. Chem. 655 (1962), 90 and ibid. 694 (1966), 78.

For the purposes of the present invention, curing agents for epoxy resins are those whose reaction with the epoxy resin is accelerated by the addition of a non-acylated imidazole. These include carboxylic acids, carboxylic anhydrides, carboxylic hydrazides, phenols, benzoguanamine and dicyanodiamide. Preferred compounds are the anhydrides of phthalic acid, tetrahydrophthalic acid, methyltetrahydrophthalic acid, hexahydrophthalic acid, pyromellitic acid and methylbicyclo[2.2.1]-heptene-2,3-dicarboxylic acid, isophthalic dihydrazide, pyrogallol, phloroglucine and, in particular, dicyanodiamide. The last-mentioned compound is virtually completely insoluble in epoxy resins and is therefore particularly useful for one-component resins having a long shelf life.

The compositions contain from 4 to 100 parts by weight of the conventional curing agent and from 0.1 to 5 parts by weight of the N-acylimidazole accelerator per 100 parts by weight of epoxy resin. In the case of bisphenol A diglycidyl ether, from 4 to 10 parts by weight of dicyanodiamide and from 0.2 to 2 parts by weight of the N-acylimidazole, or from 50 to 100 parts by weight of a carboxylic anhydride and from 0.1 to 0.5 part by weight of the N-acylimidazole, are particularly advantageous.

The curable compositions may furthermore contain conventional additives, such as pigments, fillers, reinforcing fibers, flexibilizing agents, flameproofing agents and non-volatile extenders.

The novel epoxy resin compositions are advantageously used wherever the uncured mixtures have to possess high stability, for example in casting processes using a mold. Even for the impregnation of fibrous materials, where the resin mixture must have a low viscosity and in general the procedure therefore has to be carried out at elevated temperatures, it is desirable for the impregnating resin to have a long shelf life. Mixtures of epoxy resins, dicyanodiamide and N-acylimidazoles of the formula I or II are stable for several months at room temperature and for several days at 50° C. They are very useful as impregnating resins for the production of fiber-reinforced preshapes and finished articles. Such composite fiber materials contain in general from 30 to 70 vol. % of glass fibers, carbon fibers or aramide fibers in the form of filaments, slivers, mats or woven or nonwoven fabrics.

If the novel compositions contain a solid epoxy resin, they can be processed using the reaction injection molding method. The pulverulent components are mixed, together with fillers or short fibers and pigments, and a homogeneous mass is produced by melting, allowed to cool and then milled. In this connection, it is essential that curing does not take place to any significant extent until above the melting point, which as a rule is from 50° to 100° C. In the case of conventional curing agents, which initiate the curing process even at these temperatures, the only measure which can be taken is to mill the individual components finely and then mix the powders mechanically. However, this procedure does not give adequate homogeneity.

The novel epoxy resin compositions are cured by supplying heat. The curing temperature depends on the type of epoxy resin, the type of curing agent and the type of N-acylimidazole, and can vary within wide limits from 50° to 300° C., preferably from 80° to 200° C. The preferred compositions are cured at from 120° to 160° C.

The novel compositions can be used for the production of insulating coatings, finishes, embedding materials or adhesives, or for fiber-reinforced materials.

In the Examples which follow, parts and percentages are by weight.

EXAMPLES

Preparation of the N-acylimidazole 136 g (2.0 moles) of imidazole in 1,000 ml of ether are initially taken, and 146 g (0.8 mole) of 2,4,6-trimethylbenzoyl chloride are added dropwise to the stirred mixture in the course of 30 minutes at from 10° to 20° C. Stirring is continued for 5 hours at room temperature, and the precipitated imidazole hydrochloride is filtered off under suction, the filtrate is evaporated down and the residue is distilled to give 116.4 g (68% of theory) of N-(2,4,6-trimethylbenzoyl)-imidazole of boiling point 128° C./0.01 mbar.

The following mixtures were prepared by milling the components in an agate mill:

1. 50.0 parts of Epikote 828 and
   44.5 parts of methyltetrahydrophthalic anhydride
2. 50.0 parts of Epikote 828
   44.5 parts of methyltetrahydrophthalic anhydride and
   0.25 part of an N-acylimidazole
3. 50.0 parts of Epikote 828 and
   11.5 parts of pyrogallol
4. 50.0 parts of Epikote 828 and
   11.5 parts of pyrogallol and
   0.25 part of an N-acylimidazole.

The mixtures of experiments 1 and 3 contain only conventional curing agents, without the novel N-acylimidazole as an accelerator. The results are shown in the Table.

TABLE

| Mixture | Initiation temperature | Curing time | Maximum temperature |
|---------|-----------------------|-------------|---------------------|
| C 1     | 120°                  | 90 min      | —                   |
| C 2     | 120°                  | 1.95 min    | 133°                |
| C 3     | 160°                  | 90 min      | —                   |
| C 4     | 160°                  | 1.8 min     | 237°                |

5. This Example illustrates the preparation and the curing of an epoxy resin laminate reinforced unidirectionally with glass fibers, dicyanodiamide being used as the curing agent, and the N-acylimidazole being employed as an accelerator.

62 parts of Epikote 828, 30 parts of an epoxidized novolak (Eposid 5055 from Duroplast Chemie), 8 parts of dicyanodiamide and 0.5 part of N-(2,4,6-trimethylbenzoyl)imidazole are homogenized at 80° C. This mixture has a viscosity of 2,700 mPa.s at 40° C. and has a shelf life of several months at room temperature.

To produce the laminates, the mixture is first heated to 80°–95° C. in an impregnating bath in order to obtain a viscosity sufficiently low to effect impregnation of the glass fibers, ie. from 500 to 1,000 mPa.s. Thereafter, a 1,200 tex glass roving (EC 14-P 185-1200 from GEVETEX) is drawn through the impregnating bath and then laid on a drum so that the impregnated rovings lie parallel to one another. When the winding is cut open at right angles to the fiber direction, a single-layer prepreg with a unidirectional fiber arrangement and a fiber content of about 40 vol. % is obtained. Eight such prepreg layers measuring 250×400 mm are laid one on top of the other, with the fibers oriented in the same direction, and are introduced into a sheet mold which has a mold opening of 2 mm and has been preheated to 80° C. The ram is then brought to its end position in the course of 15 minutes, the mold temperature is increased to 150° C. and the prepreg stack is cured in the course of 30 minutes to give the laminate. After cooling and demolding, the laminate is post-cured for 60 minutes at 170° C.

The glass content of the laminate is 65% by weight, and the thermal and mechanical properties are summarized below.

| | |
|---|---|
| Tensile strength parallel to the fiber direction | 1,020 N/mm$^2$ |
| Tensile modulus of elasticity parallel to the fiber direction | 33,800 N/mm$^2$ |
| Elongation at break parallel to the fiber direction in the tensile test | 3.0% |
| Tensile strength at right angles to the fiber direction | 64 N/mm$^2$ |
| Tensile modulus of elasticity at right angles to the fiber direction | 11,300 N/mm$^2$ |
| Elongation at break at right angles to the fiber direction in the tensile test | 0.7% |
| Glass transition temperature (torsional vibration analysis) | 150° C. |

We claim:

1. A curable resin composition containing
   A. 100 parts by weight of an epoxy resin,
   B. from 4 to 100 parts by weight of a conventional curing agent for epoxy resins, and
   C. from 0.1 to 5 parts by weight of a N-acylimidazole as an accelerator, wherein component C is an N-acylimidazole of the formula

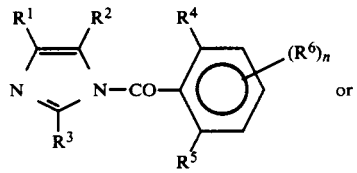

or

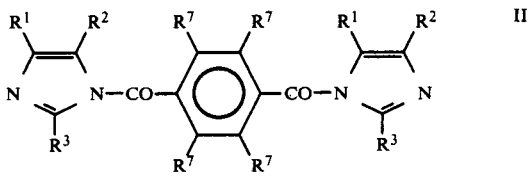

where $R^1$, $R^2$ and $R^3$ can be identical or different and are each hydrogen, branched or straight-chain alkyl of 1 to 17 carbon atoms, chlorine, or phenyl which is unsubstituted or substituted by alkyl, alkoxy or chlorine, or are each haloalkyl, hydroxyalkyl, a carboxylic ester group or a carboxamide group, $R^4$ and $R^5$ can be identical or different and are each a branched or straight-chain alkyl, alkoxy or alkylthio group of 1 to 4 carbon atoms, $R^6$ is hydrogen, an alkoxy or alkylthio group of 1 to 6 carbon atoms, dialkylamino where alkyl is of 1 to 6 carbon atoms or branched or straight-chain alkyl of 1 to 12 carbon atoms, n is 1, 2 or 3 and $R^7$ is alkyl of 1 to 4 carbon atoms.

2. A curable composition as claimed in claim 1, which contains
   A. 100 parts by weight of bisphenol A diglycidyl ether as an epoxy resin
   B. from 4 to 10 parts by weight of dicyanodiamide as a curing agent for the epoxy resin, and
   C. from 0.2 to 2 parts by weight of an N-acylimidazole.

3. A process for the production of a molding by introducing a curable composition as claimed in claim 1 into a mold, and carrying out curing at from 50° to 300° C.

4. A process for the production of a finish, a coating or an adhesive by applying a curable composition as claimed in claim 1 onto a substrate, and carrying out curing at from 50° to 300° C.

5. A process for the production of a composite fiber material by impregnating from 30 to 70 vol. % of reinforcing fibers with from 70 to 30 vol. % of a curable composition as claimed in claim 1, and carrying out curing at from 50° to 300° C.

6. A curable resin composition as set forth in claim 1, wherein $R^4$ and $R^5$ are each alkyl of 1 to 4 carbon atoms.

7. A curable resin composition as set forth in claim 1, wherein $R^4$ and $R^5$ are each methyl.

* * * * *